(12) United States Patent
Sun et al.

(10) Patent No.: US 11,478,208 B2
(45) Date of Patent: Oct. 25, 2022

(54) X-RAY IMAGE QUALITY CONTROL SYSTEM

(71) Applicant: CARESTREAM HEALTH, INC., Rochester, NY (US)

(72) Inventors: Ken Sun, Shanghai (CN); Mingzhi Chen, Shanghai (CN); Xinyu Zhang, Beijing (CN); Jing Zhang, Shanghai (CN); Minggang She, Shanghai (CN)

(73) Assignee: Carestream Health, Inc., Rochester, NY (US)

( * ) Notice: Subject to any disclaimer, the term of this patent is extended or adjusted under 35 U.S.C. 154(b) by 210 days.

(21) Appl. No.: 16/940,555

(22) Filed: Jul. 28, 2020

(65) Prior Publication Data

US 2021/0321968 A1  Oct. 21, 2021

(51) Int. Cl.
*A61B 6/00* (2006.01)
*G06T 7/00* (2017.01)
*A61B 6/03* (2006.01)

(52) U.S. Cl.
CPC ........... *A61B 6/5211* (2013.01); *A61B 6/03* (2013.01); *G06T 7/0012* (2013.01); *G06T 2207/10081* (2013.01); *G06T 2207/30168* (2013.01)

(58) Field of Classification Search
CPC ....... A61B 6/5211; A61B 6/03; A61B 6/5258; G06T 7/0012; G06T 2207/10081; G06T 2207/30168; G06T 2207/10116; G06T 7/0002; G06T 7/11; G06T 2207/201; G06N 20/00; G16H 30/20
See application file for complete search history.

(56) References Cited

U.S. PATENT DOCUMENTS

| | | | |
|---|---|---|---|
| 2008/0242968 A1* | 10/2008 | Claus | G06V 10/10 600/407 |
| 2010/0086189 A1* | 4/2010 | Wang | G06T 5/00 340/600 |
| 2014/0146950 A1* | 5/2014 | Chida | A61B 6/583 378/207 |
| 2015/0342550 A1* | 12/2015 | Lee | A61B 6/5205 378/62 |
| 2017/0224302 A1* | 8/2017 | Von Berg | A61B 6/466 |
| 2020/0402229 A1* | 12/2020 | Chen | G06T 7/11 |

\* cited by examiner

*Primary Examiner* — Molly Wilburn

(57) ABSTRACT

An X-ray image quality control system includes an image acquisition unit configured to acquire an X-ray image and determine the type of imaged body part and the type of projection mode. A quality detection unit is configured to detect an image defect in X-ray image with regard to the type of the imaged body part and/or the type of the projection mode. The quality control system effectively identifies image defects including inaccurate positioning, patient movement, external object artifacts, and poor exposure. The system provides feedback to the technician at the image acquisition point to adjust the image acquisition solution in a timely manner.

18 Claims, 1 Drawing Sheet

X-RAY IMAGE QUALITY CONTROL SYSTEM

CROSS REFERENCE TO RELATED APPLICATIONS

This patent application claims the benefit of and is a U.S. national filing of Chinese Patent Application Invention No. 202010311001.3, filed Apr. 20, 2020, in the name of Sun et al., and entitled METHOD AND SYSTEM FOR AUTOMATIC QUALITY CONTROL FOR DR IMAGES, which is hereby incorporated by reference herein in its entirety.

TECHNICAL FIELD

The present disclosure relates to the technical field of digital X-ray imaging, and more particularly, to an X-ray image quality control system.

TECHNICAL BACKGROUND

In digital X-ray imaging, images with poor quality are often unacceptable. The reasons may include incorrectly positioning of the imaged body part, patient movement, artifacts, and poor exposure. Among them, positioning errors can be divided into two types: center positioning errors and errors caused by improper projection, such as the rotation of the camera. The positioning error may also include errors such as the body part to be imaged is not completely imaged (or is blocked or truncated).

Quality control for X-ray images (such as digital radiography images or computed radiography images) is usually implemented based on the visual observation of a technician, which appears to be relatively subjective. Some image quality defects are relatively obvious, such as necklace shadows (which will block the observation of the chest or spine) or visual truncation of the soft tissue region of the knee. Some image quality defects, such as the area of the overlap region between the scapula and lungs exceeds a predetermined threshold, are relatively difficult to be identified and often require careful observation. In general, the quality control of X-ray images requires manual operation, and is subjective and highly depends on the professional experience of technicians.

An automated image quality assurance system includes motion detection, anatomical integrity detection, low exposure detection, and artifact detection. The image quality assurance system of the prior art may have the following defects: no special image quality standard is adopted in the solution for the detection of incorrectly positioning, and the solution for the detection of poor exposure may depend on the exposure index or a global or local histogram analysis, and the image quality assurance system does not consider whether the DR imaged body parts, tissues or bone structure can be identified. In another image quality assessment solution, the DR image is uploaded to the cloud service, and the image quality assessment is performed by the server of the cloud service. However, the technicians at the image acquisition side cannot get feedback in time to adjust the image acquisition solution.

SUMMARY OF THE INVENTION

According to one aspect of the present disclosure, an X-ray image quality control system is provided, which overcomes at least one of the above-mentioned defects of the prior art.

In order to achieve the above object, the present disclosure provides a technical solution as follows.

An X-ray image quality control system includes: an image acquisition unit configured to acquire an X-ray image and determine the type of the imaged body part and the type of the projection mode; a quality detection unit configured to detect an image defect in X-ray image with regard to the type of the imaged body part and/or the type of the projection mode.

Alternatively, the quality control system further comprises a quality feedback unit configured to feed back image defects to the image acquisition unit and/or the image acquisition side.

Alternatively, the quality detection unit is configured to extract a feature set of the position and orientation for a bone structure and/or a soft tissue structure of the imaged body part; locate or segment a region of interest of the imaged body part based on the calculation of the feature set.

Alternatively, the quality detection unit is configured to be trained using a machine learning algorithm to determine and/or adjust at least a first detection parameter.

Alternatively, the quality detection unit is configured to, for a first combination of the type of the imaged body part and the type of the projection mode, detect the region of interest based on the first detection parameter; for a second combination of the type of the imaged body part and the type of the projection mode, detect the region of interest based on a second detection parameter different from the first detection parameter.

Alternatively, the quality detection unit is further configured to detect the region of interest associated with a first image defect type by using a histogram analysis algorithm.

Alternatively, the image acquisition unit is configured to perform pre-processing on the X-ray image, the pre-processing comprises dividing the X-ray image into a bone structure region, a soft tissue region and a background region.

Alternatively, the quality feedback unit comprises an interactive unit for selecting image defects and/or setting an automatic selection parameters.

The present disclosure further provides an X-ray imaging apparatus, which includes the above-mentioned X-ray image quality control system.

According to another aspect of the present disclosure, an X-ray image quality detection method is provided, comprising: acquiring an X-ray image; determining the type of the imaged body part and the type of the projection mode; detecting an image defect of the X-ray images with regard to the type of the imaged body part and/or the type of the projection mode.

Alternatively, the quality detection method further includes feeding the image defect back to an X-ray image acquisition side.

Alternatively, detecting the image defect of the X-ray image comprises: extracting a feature set of the position and orientation for a bone structure and/or a soft tissue structure of the imaged body part; locating or segmenting a region of interest of the imaged body part based on the calculation of the feature set.

Alternatively, detecting the image defect of the X-ray image further comprises: for a first combination of the type of the imaged body part and the type of the projection mode, detecting the region of interest based on a first detection parameter; for a second combination of the type of the imaged body part and the type of the projection mode, detecting the region of interest based on a second detection parameter different from the first detection parameter;

wherein the first detection parameter and the second detection parameter are determined by using a machine learning algorithm.

Alternatively, detecting the image defect of the X-ray image further comprises detecting the region of interest associated with a first image defect type by using a histogram analysis algorithm.

Alternatively, the method further comprises: performing pre-processing on the X-ray image, wherein the pre-processing comprises dividing the X-ray image into a bone structure region, a soft tissue region, and a background region.

The present disclosure provides an automated image quality control system, which automatically and comprehensively evaluates the quality of X-ray images, and identifies image defects including inaccurately positioning, patient movement, external object artifacts, and poor exposure. The image quality control system further provides feedback to technicians at the image acquisition point, which is beneficial for a timely adjustment of the image acquisition solution. In addition, the system can also use machine learning techniques to evaluate X-ray image quality in real time.

DESCRIPTION OF EMBODIMENTS

More specific details are presented in the following description in order to provide a thorough understanding of the present disclosure. However, those skilled in the art will clearly know that embodiments of the present disclosure can be implemented even without these specific details. In the present disclosure, specific numerical references are used, such as "first element", "second device" and so on. However, the specific numerical references should not be interpreted as having to obey their literal order, but rather indicate that "first element" and "second element" are different.

The specific details proposed by the present disclosure are only exemplary, and the specific details may vary, but still fall within the spirit and scope of the present disclosure. Throughout the disclosure, the term "couple" means being directly connected to a component or indirectly connected to a component via another component.

In the present disclosure, the X-ray image is a digital image obtained by a flat panel detector after the X-rays emitted by the X-ray source pass through the human body. Depending on the types of the flat panel detector structure and the imaging technology, "projection mode" can be classified into direct digital X-ray imaging (amorphous selenium), indirect digital X-ray imaging (amorphous silicon), CCD line imaging, multi-wire proportional ionization chamber imaging. In the present disclosure, the imaged body part may be the chest spine, dorsal spine, elbows, and the knees. Various imaged body parts may have distinct bone structures and tissue structures.

Preferred embodiments of the method, system, and apparatus which are suitable for implementing the present disclosure are described below by reference to the drawings.

Although the embodiments are described with regard to a single combination of elements, it should be understood that the present disclosure includes all possible combinations of the disclosed elements. Therefore, if one embodiment includes elements A, B, and C, and the second embodiment includes elements B and D, the disclosure should also be deemed as including other remaining combinations of A, B, C, or D, even if not explicitly disclosed.

Figure 1:
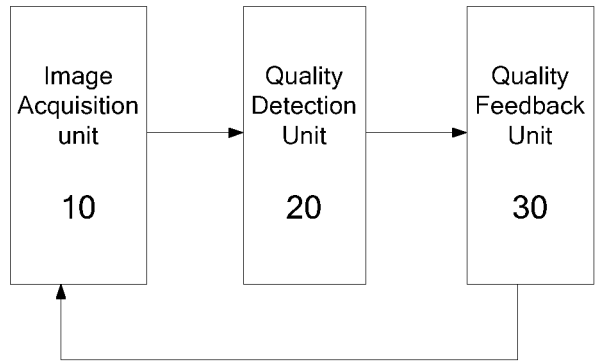
FIG. 1 shows a schematic diagram of a module structure of an image quality control system provided by a first embodiment of the present disclosure.
Figure 2:
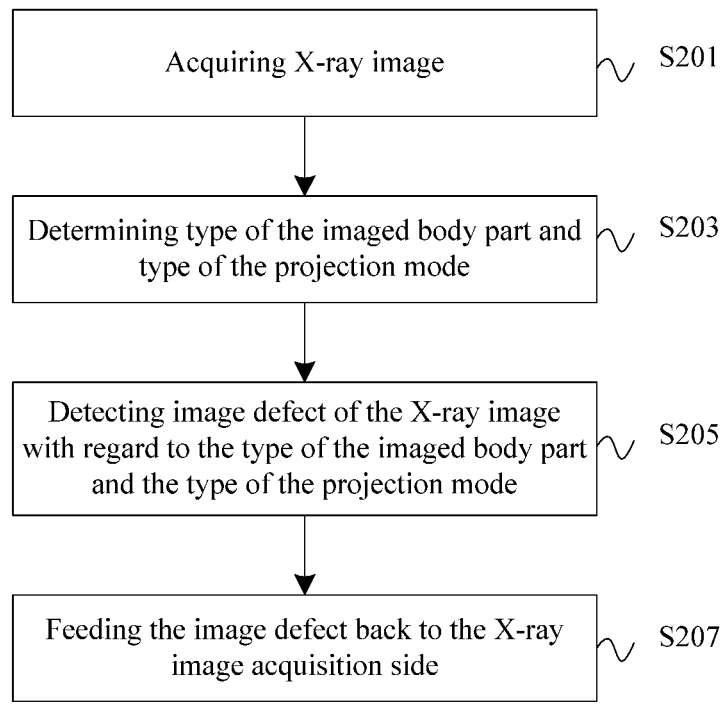
FIG. 2 shows a schematic flowchart of an X-ray image quality feedback method provided by a second embodiment of the present disclosure.

As shown in FIG. 1, a first embodiment of the present disclosure provides an X-ray image quality control system, which includes an image acquisition unit 10, a quality detection unit 20, and a quality feedback unit 30.

The image acquisition unit 10 is configured to acquire X-ray images, determine the type of the imaged body part and the type of the projection mode, the image acquisition unit 10 is coupled to the quality detection unit 20 and provides X-ray images to it. The quality detection unit 20 is configured to detect image defects in the X-ray image with regard to the type of the imaged body part and/or the type of the projection mode, and the quality detection unit 20 is coupled to the quality feedback unit 30 and provides quality detection results thereto. The quality feedback unit 30 is configured to feedback image defects to the image acquisition unit 10 so as to form a closed control loop. It should be understood that, in addition to detecting defects, the quality detection unit 20 may also be used to detect some regions or features with which users may be interested or concerned, and the quality detection results may include the detection results of defects, regions of interest, or features of interest.

In some embodiments of the present disclosure, the X-ray image quality control system includes an image acquisition unit that acquires an X-ray image from an external image data source. In other embodiments, the image acquisition unit may acquire X-ray images from an external data source (for example, a medical cloud server or a hospital data center), or may use an image acquisition device included in the image acquisition unit to acquire X-ray images. In response, the quality feedback unit may feedback the quality detection result to the image acquisition unit or the image acquisition side.

In this control system, the process of quality detection is performed by the quality detection unit 20 arranged at the local side of the system, and there is no need to upload X-ray image data to the cloud server, and there is no need to obtain the detection result data from the cloud server. In this way, the feedback of the image defect transmitting from the quality feedback unit 30 to the image acquisition unit 10 can be achieved in nearly real time, so that the technician at the image acquisition side can adjust the acquisition solution in time to overcome the image defect and reacquire the desired X-ray image. In other embodiments of the present disclosure, the above-mentioned quality feedback step is not necessary, and the technician can voluntarily obtain improvement suggestions from the quality detection unit.

In some embodiments of the present disclosure, the type of imaged body part is the chest spine, the type of projection mode is direct digital X-ray imaging. The type of imaged body part may be the front of the knee, and the type of projection mode is CCD line imaging. It should be understood that various types of the imaged body parts and types of the projection modes may form multiple combinations. Meanwhile, bone structures and soft tissue structures of different imaged body parts can be significantly distinct from each other. For example, there is no spine structure in the front of the knee, and there is no intra-articular meniscus in the thoracic spine. In addition, under different projection modes, the X-ray images of the same imaged body part may vary greatly.

In order to accurately identify possible image defects in different imaged body parts, the quality detection unit 20 extracts a set of the features of the position and orientation of the bone structure and soft tissue structure in the imaged body part, and locates or segments the regions of interest (ROIs) in the imaged body part based on the calculation of the feature set. Each ROI may correspond either to a distinguishable bone structure region or soft tissue region, or to an abnormal part in the X-ray image, i.e., an image defect. The portion of the image outside the ROIs can be deemed as the background portion of the image. The ROIs may also include a combination of several bone structure regions or a combination of bone structure regions and appropriate soft tissue regions. In the subsequent steps, the ROIs will be further classified into normal ROI and abnormal ROI. The abnormal ROI corresponds to various kinds of image defects. The classification of the ROIs is also based on the features extracted from the ROIs. The image block of a ROI is provided to the detection network in the quality detection unit 20 together with the features extracted therefrom. The detection network performs defect detection based on the result of location and segmentation. The method for the detection includes threshold method, template matching, image classification, or a combination thereof.

The present disclosure uses a machine learning algorithm or a deep learning method to train the quality detection unit 20. The quality control technician may provide the quality detection unit 20 with various X-ray images including normal X-ray images and abnormal X-ray images (including one or more image defects) for the steps of training and learning. One or more detection networks are provided in the quality detection unit 20, and each detection network has multiple adjustable parameters. Through training and learning, the quality detection unit 20 has a high sensitivity to various image defects. According to the present disclosure, there are many types of X-ray image defects. For example, a first image defect type includes exposure artifacts and motion artifacts, and a second image defect type includes placement defects and projection defects.

In a more preferred embodiment, for each of the combinations of the imaged body part type and projection mode type, the quality detection unit 20 is configured to train the detection networks using a machine learning algorithm to obtain a corresponding set of recognition parameters. In this way, each set of identification parameters is dedicated to a combination of the imaged body part type and projection mode type, so that it may have a higher sensitivity to various types of image defects in the X-ray image obtained under this combination. To this end, the present disclosure adopts different (preferably unique) detection parameters to detect each ROI with regard to various combinations of the type of the imaged body parts and the type of the projection mode, which is beneficial to improve the accuracy of detection and is applicable for a wider range of X-ray-based detection applications.

Specifically, with regard to the first combination of the type of imaged body part and the type of projection mode, the quality detection unit 20 detects the region of interest by using a first detection parameter(s). As for the second combination of the type of the imaged body part and the type of projection mode, a second detection parameter (s) different from the first detection parameter(s) can be used to detect the region of interest. The first detection parameter(s) is at least partially different from the second detection parameter (s). Similarly, for the third combination of the type of imaged body part and the type of projection mode, the quality detection unit 20 selects a third detection parameter (s) to perform detection. Accordingly, the detection networks in the quality detection unit 20 can have a one-to-one correspondence with the above detection parameters so as to facilitate a separate step of training and learning, or each unique combination of the detection networks can correspond to the detection parameter(s) to achieve the reuse of resources.

After the training of the quality detection unit 20 is completed, on the basis of the imaging standards (including the specific requirements for the imaged body part and the projection mode) and the above-mentioned classification data, the quality detection unit implemented on a computer or a processor is used to perform quality detection on the acquired X-ray image to separate erroneous images from normal images. Error images containing various image defects can be provided to technical experts.

In some embodiments of the present disclosure, the quality detection unit 20 also adopts a histogram analysis algorithm to detect the region(s) of interest associated with an image defect type (e.g., exposure artifacts or underexposure, overexposure issues). This is because histogram analysis has a good degree of recognition for artifact-like defects. The histogram analysis algorithm can be combined with the above machine learning algorithm to jointly identify various types of image defects in X-ray images.

In some embodiments of the present disclosure, the image acquisition unit 10 also performs pre-processing on the collected X-ray image, including segmenting the X-ray image into a bone structure region, a soft tissue region, and a background region. X-ray images that do not meet the pre-processing requirements will be rejected for subsequent processing. For example, images that cannot be segmented into bone structure regions or soft tissue regions clearly do not meet the requirements, and the images in which the distance between identifiable bone structure regions (not necessarily the true bone structure regions) is too close or too far, which may imply that a necklace or other body part possibly blocks the imaged body part, do not conform to the requirements either. The preprocessing can speed up the execution efficiency of the subsequent steps, so that the X-ray image quality control system can better conform to the real-time requirements.

The quality feedback unit 30 feeds back the detected image defect to the image acquisition unit 10. As an example, the quality feedback unit provides text/color hints to technical experts, and marks the defect position/size through a heat map or a box or by other means. Different defects can be represented as boxes of different colors. The quality feedback unit 30 may further include an interactive unit, through which the technical expert can screen out image defects for feedback or set selecting parameter(s) to automatically select the types of image defects that meet the feedback requirements. Preferably, the quality feedback unit 30 is further configured to provide the image acquisition side or the image acquisition unit 10 with an indication about how to improve the X-ray image acquisition, for example, to instruct adjustment of the projection direction or exposure parameters of the X-ray source, and instruct removal of the patient's necklace etc.

Some embodiments of the present disclosure provide an X-ray imaging apparatus, which is used for X-ray imaging of a patient's body part. The imaging apparatus is provided with an image quality control system of the first embodiment as mentioned above.

A second embodiment of the present disclosure provides an X-ray image quality feedback method, which includes steps S201-S203-S205-S207. This quality feedback method is performed on the local side of the system (such as the X-ray image acquisition side) without the requirement of uploading the X-ray image data to the cloud server.

In step S201, an X-ray image (for example, a DR image) is acquired. In step S203, the type of imaged body part and the type of projection mode can be determined. In step S205, image defects in the DR image are detected with regard to the type of imaged body part and the type of projection mode. In step S207, the image defects are fed back to the DR image acquisition side. Some of the above steps may be split, combined with each other, or executed in a different order. For example, steps S201 and S203 may be combined into one step, and step S207 may be performed before step S201.

In some embodiments of the present disclosure, the DR image is not obtained through the acquisition process, but comes from an external image data source, for example, including a medical cloud server or a hospital data center. In addition, as an optional step, the step S207 of feeding back the image defects may be omitted in some embodiments. When step S207 is adopted, various quality detection results including image defects can be fed back to the image acquisition side, medical cloud server or hospital data center for evaluation or improvement.

Detecting image defects in the DR image includes determining the ROIs, including: extracting the set of features of the location and orientation of the bone structure and soft tissue structure in the imaged body part; based on the calculation of the set of features, locating or segmenting the regions of interest of the imaged body part.

In the subsequent steps, the ROIs will be further classified into normal ROI(s) and abnormal ROI(s). The normal ROI may correspond to a bone structure region, a soft tissue region, or a combination of the bone structure regions, or a combination of a bone structure region and an appropriate soft tissue region. The abnormal ROI may correspond to various types of image defects. The image defects detected in step S205 will be fed back to the DR image acquisition side in step S207, and further improvement instructions can be provided for an operator at the image acquisition side to adjust the acquisition solution.

In the process of using machine learning algorithms to train the quality detection unit, wireless radiological operators and technical experts may provide and evaluate diagnostic images, including defective X-ray images, involving various image quality defects. These image quality defects include but are not limited to incorrect positioning, patient movement, incorrect exposure, and artifacts. Technical experts classify and label the evaluated images for use by the training of the quality detection unit. The classification or the added label should be associated with the type of imaged body part and/or the type of projection mode. Training the quality detection unit in this way makes it more sensitive to the type of the imaged body part and the type of the projection mode. In other words, for different types of imaged body parts, the detection parameters used by the quality detection unit are different from each other; but for the same type, the detection parameters will be substantially the same. In addition, for different types of projection modes, the parameters used by the quality detection unit will vary greatly, but the detection parameters for the same type of projection mode tend to be consistent with each other.

In some embodiments of the present disclosure, detecting the image defect in the X-ray image further includes: for a first combination of the type of imaged body part and the type of projection mode, detecting the region(s) of interest based on a first detection parameter determined by a machine learning algorithm; for the second combination of the type of imaged body part and the type of projection mode, detecting the region(s) of interest based on a second detection parameter different from the first detection parameter, and the second detection parameter is also determined by a machine learning algorithm. In this way, a set of identification parameters is dedicated to a combination of imaged body part type and projection mode type, which helps achieve high accuracy in identifying image defects.

Histogram analysis algorithms can also be used to detect image defects, which have a good degree of recognition for defects such as exposure artifacts.

In some embodiments, in order to improve processing efficiency, the collected X-ray image is pre-processed. The pre-processing may divide the X-ray image into a bone structure region, a soft tissue region, and a background region.

Those skilled in the art will understand that the various illustrative logical blocks, modules, circuits, and algorithm steps described in connection with the aspects disclosed herein may be implemented as electronic hardware, computer software, or a combination of both. To illustrate the interchangeability between hardware and software, various illustrative components, blocks, modules, circuits, and steps have been described above generally based on their functionalities. Whether the functionalities are implemented as hardware or software will depend on the particular application and design constraints imposed on the overall system. The skilled artisans can implement the described functionalities in a varying manner for a specific application, but such implementation decision should not be understood as departing from the scope of the present disclosure.

The above description is only for the preferred embodiments of the present disclosure, and is not intended to limit the protection scope thereof. Those skilled in the art may make various modified designs without departing from the concept of the present disclosure and the accompanying claims. Thus, any embodiment or modified design based on the spirit of the application can be naturally extended to other medical imaging quality control technologies.

What is claimed is:

1. An X-ray image quality control system comprising:
    an image acquisition unit configured to acquire Drill a digital X-ray image of a patient anatomy under control of a technician, to determine which body part is captured in the imaged patient anatomy, and to determine the type of the projection mode used to capture the imaged patient anatomy including a projection direction of the X-ray projection relative to the patient anatomy; and
    a quality detection unit configured to detect an image defect in the X-ray image of the patient anatomy with regard to the body part that is captured therein and with regard to the direction of the X-ray projection relative to the patient anatomy;
    the quality detection unit further configured to use a first detection parameter to detect a defect in the imaged patient anatomy in response to the image acquisition unit determining that the imaged patient anatomy is a first body part and that the projection mode used to capture the imaged patient anatomy included a first projection direction, the quality detection unit further configured to use a second detection parameter different from the first detection parameter to detect a defect in the imaged patient anatomy in response to the image acquisition unit determining that the imaged patient anatomy is a second body part different from the first body part and that the projection mode used to capture the imaged patient anatomy included a second projection direction different from the first projection direction.

2. The control system according to claim 1, further comprising:
a quality feedback unit, configured to feed back the detected image defect to the image acquisition side for use by the technician to correct an image capture configuration.

3. The control system according to claim 1, wherein the quality detection unit is configured to:
extract a feature set of the location and orientation for a bone structure and/or a soft tissue structure of the imaged patient anatomy; and
locate or segment a region of interest of the imaged patient anatomy based on the extracted feature set.

4. The control system according to claim 2, wherein the quality detection unit is configured to be trained using a machine learning algorithm to determine and/or adjust at least the first detection parameter.

5. The control system according to claim 4, wherein the quality detection unit is configured to:
for a first combination of the type of the captured body part and the type of the projection mode, detect a region of interest based on the first detection parameter; and
for a second combination of the type of the captured body part and the type of the projection mode, detect the region of interest based on a second detection parameter different from the first detection parameter.

6. The control system according to claim 2, wherein the quality detection unit is further configured to detect a region of interest associated with a first image defect type by using a histogram analysis algorithm.

7. The control system according to claim 2, wherein the image acquisition unit is further configured to perform pre-processing on the acquired X-ray image of the patient anatomy, the pre-processing comprises dividing the acquired X-ray image into a bone structure region, a soft tissue region and a background region.

8. The control system according to claim 2, wherein the quality feedback unit is further configured to select the image defect and mark the image defect for use by the technician.

9. The control system according to claim 1, wherein the image acquisition unit is further configured to receive the X-ray image of the patient anatomy from an external image data source.

10. The control system according to claim 1, wherein the image acquisition unit comprises an image acquisition device configured to acquire the X-ray image.

11. A computer implemented X-ray image quality detection method, the method comprising:
receiving a digital X-ray image of a part of a body;
determining what body part is captured in the X-ray image and the direction of the X-ray projection, relative to the body, used to capture the X-ray image; and
detecting an image defect of the X-ray image using a first detection parameter in response to determining that the X-ray image captured a first body part and that the direction of the X-ray projection used to capture the X-ray image included a first projection direction, or detecting an image defect of the X-ray image using a second detection parameter in response to determining that the X-ray image captured a second body part different from the first body part and that the direction of the X-ray projection used to capture the X-ray image included a second projection direction different from the first projection direction.

12. The method of claim 11, further comprising:
feeding the detected image defect back to an X-ray image acquisition side.

13. The method of claim 11, wherein detecting the image defect of the X-ray image comprises:
extracting a feature set of a location and orientation for a bone structure and/or a soft tissue structure of the captured body part; and
locating or segmenting a region of interest of the captured body part based on the extracted feature set.

14. The method of claim 13, wherein detecting the image defect of the X-ray image further comprises:
for a first combination of the captured body part and the direction of the X-ray projection, detecting the region of interest based on the first detection parameter;
for a second combination of the captured body part and the direction of the X-ray projection, detecting the region of interest based on a second detection parameter different from the first detection parameter; and
wherein the first detection parameter and the second detection parameter are determined by using a machine learning algorithm.

15. The method of claim 11, wherein detecting the image defect of the X-ray image further comprises detecting a region of interest associated with a first image defect type by using a histogram analysis algorithm.

16. The method of claim 11, further comprising:
performing pre-processing on the X-ray image, wherein the pre-processing comprises dividing the X-ray image into a bone structure region, a soft tissue region and a background region.

17. A computer-readable storage medium having stored thereon non-transitory machine-executable instructions, wherein the non-transitory machine-executable instructions, when executed by a processor, implement the method of claim 11.

18. The control system according to claim 8, wherein the quality feedback unit is further configured to mark the image defect as a box.

* * * * *

UNITED STATES PATENT AND TRADEMARK OFFICE
CERTIFICATE OF CORRECTION

| | | |
|---|---|---|
| PATENT NO. | : 11,478,208 B2 | Page 1 of 1 |
| APPLICATION NO. | : 16/940555 | |
| DATED | : October 25, 2022 | |
| INVENTOR(S) | : Ken Sun et al. | |

It is certified that error appears in the above-identified patent and that said Letters Patent is hereby corrected as shown below:

In the Claims

Column 8, Claim 1, Line 46 — Please replace "an image acquisition unit configured to acquire Drill a" with --an image acquisition unit configured to acquire a--

Signed and Sealed this
Sixth Day of December, 2022

Katherine Kelly Vidal
*Director of the United States Patent and Trademark Office*